United States Patent [19]

Brueggemann et al.

[11] Patent Number: 6,051,317
[45] Date of Patent: Apr. 18, 2000

[54] SHEET-LIKE SUPERABSORBENT STRUCTURES

[75] Inventors: Helmut Brueggemann, Duisburg; Kurt Dahmen, Moenchengladbach; Dieter Lehwald, Koeln; Roland Theilmann, Krefeld, all of Germany

[73] Assignee: Stockhausen GmbH & Co. KG, Krefeld, Germany

[21] Appl. No.: 08/894,475

[22] PCT Filed: Feb. 14, 1996

[86] PCT No.: PCT/EP96/00621

§ 371 Date: Dec. 22, 1997

§ 102(e) Date: Dec. 22, 1997

[87] PCT Pub. No.: WO96/25959

PCT Pub. Date: Aug. 29, 1996

[30] Foreign Application Priority Data

Feb. 20, 1995 [DE] Germany .................. 195 05 708

[51] Int. Cl.[7] .................. A61L 15/60; C08J 5/18; B32B 5/18

[52] U.S. Cl. .................. 428/378; 428/393; 428/394; 428/396; 442/60; 442/61; 442/62; 442/64; 442/70; 442/72; 442/76; 442/117; 442/164; 442/166; 442/167; 442/63; 604/304; 604/365; 604/366; 604/367; 604/372; 604/374; 604/377; 604/378; 47/1.01 R; 52/319; 53/111 RC; 239/34; 239/44

[58] Field of Search .................. 428/378, 393, 428/394, 396; 442/60, 61, 62, 63, 64, 70, 72, 76, 117, 164, 166, 167; 604/304, 365, 366, 367, 372, 374, 377, 378; 47/1.01 R; 52/319; 53/111 RC; 239/34, 44

[56] References Cited

U.S. PATENT DOCUMENTS

| 4,335,722 | 6/1982 | Jackson | 128/285 |
| 5,246,770 | 9/1993 | Bottiglione et al. | 428/244 |
| 5,589,256 | 12/1996 | Hansen et al. | 428/283 |
| 5,693,411 | 12/1997 | Hansen et al. | 428/283 |

FOREIGN PATENT DOCUMENTS

WO 94/25519  11/1994  WIPO.

*Primary Examiner*—Nathan M. Nutter
*Attorney, Agent, or Firm*—Evenson, McKeown, Edwards & Lenahan, P.L.L.C.

[57] ABSTRACT

The invention relates to sheet-like absorbents for water and aqueous solutions, containing at a defined distribution A) at least one water-swellable synthetic and/or natural superabsorbent polymer, and B) at least one water-soluble synthetic and/or natural polymer as a matrix of sheet-like design wherein the superabsorbent component A) is integrated or fixed. The sheet-like absorbents have an increased absorptive capacity for water and aqueous liquids, particularly under load. They are manufactured by forming a sheet-like matrix from the water-soluble synthetic and/or natural polymers B) and providing same with said water-swellable synthetic and/or natural superabsorber A), e.g., by applying a solution of matrix B) on a surface, sprinkling same with component A), and drying the sheet-like structure thus obtained. Such sheet-like absorbents are used in hygienic articles, as components in natural or artificial soils, as insulating material for pipes and lines, primarily cables and building constructions, as liquid-absorbing and liquid-storing component in packaging materials, as a part in articles of clothing, and as a depot for the controlled release of an active substance.

43 Claims, 1 Drawing Sheet

SHEET-LIKE SUPERABSORBENT STRUCTURES

The invention relates to sheet-like absorbents for water and aqueous solutions, a process for the production of said sheet-like absorbents, and their use.

Sheet-like absorbents present the possibility of fixing superabsorbent polymers (SAP) in the form of a powder or granulate in any desired arrangement in/on one or multiple sheets. Said fixation is then carried out in the optimum form for later use, such as in diapers for babies, adult incontinence articles, cable sheathings, soil conditioners, packaging inserts in the food industry, for animal hygiene, wound dressings, and cloths.

For later use, in order to achieve optimum distribution of a powdered superabsorbent polymer and to fix same, various methods have been described.

EP 212,618 B1 describes diaper constructions wherein polymerizates having a specific grain size distribution are distributed in a cellulose fiber layer. However, such a construction is insufficiently stable with respect to the distribution of the superabsorbent polymer; in particular, the distribution of the SAP may be altered undesirably during transportation, resulting in non-uniform absorption, e.g., in a diaper.

Another method of fixing powdered superabsorbent polymers in a specific arrangement is described in EP 425,269 A2, according to which the SAPs are bound to thermoplastic, water-insoluble fibers. Binding the SAP to the fiber is effected in such a way that a slightly surface-melted fiber is contacted with the powdered superabsorbent polymer. The fibers themselves are fixed among one another in the same manner. The disadvantage of this process is that the absorptive capacity of the powdered superabsorbent polymer is not utilized in full extent. Part of the SAP is covered by the thermoplastic and thus not reached by water or aqueous solutions.

EP 547,474 A1 describes a process for the production of absorbing materials wherein superabsorbent polymers are distributed. The absorptive capacity of the absorbing materials thus obtained is lower than the ratio of SAP incorporated in these materials would suggest, i.e., part of the SAP is blocked as a result of the selection of materials used and the production process employed. Moreover, the type of matrix material used is limited in that the melting point of this material must be above the decomposition temperature of the SAP.

EP 303,445 A1 describes an absorbent sheet material wherein a water-containing SAP has been fixed on a support. The use of this structure is limited to a patch used as drug reservoir.

JP Application No. 75-85462 describes a method of producing superabsorbent sheets made of a starch/graft polymer integrated in a water-soluble, film-forming polymer.

As an indispensable third component, this document mentions a material serving as base material. The superabsorbent polymer is fixed on said base material together with the soluble, film-forming polymer.

EP 604,730 A1 describes SAP-containing structures which decompose in water. In addition to the SAP, dispersible polymers and plasticizers are mentioned as indispensable components. The structures manufactured according to this application do by no means meet the demand for a defined arrangement of a superabsorber in a matrix, because the methods described in this document, such as extrusion, mixing or blending, are absolutely unsuitable for this purpose.

After disintegration of the described sheet materials, particles remain in addition to the superabsorber; consequently, the matrix material is not soluble in water.

It is therefore the object of the present invention to provide a superabsorbent sheet having a defined arrangement of superabsorbent polymers at full utilization of the swelling capacity of the superabsorbent polymers, i.e., without loss of absorptive capacity.

It is another object of the invention to find production processes according to which such a sheet can be manufactured in an uncomplicated and cost-effective way. In addition, the sheet should not be fixed to a substrate, as described in the Japanese patent application No. 75-85462, so that such a sheet can be used more universally.

Said object is achieved by a sheet-like absorbent structure for water or aqueous liquids, containing A) at least one water-swellable synthetic and/or natural polymer and B) at least one water-soluble synthetic and/or natural polymer, wherein component A is integrated or fixed in a defined fashion in matrix component B having sheet-like design.

This combination does not reduce the absorptive capacity of the superabsorbent polymer, since the matrix dissolves on contact with water or aqueous liquids and therefore, does not impede swelling of the SAP. This embodiment permits controlling the absorption rate for water or aqueous liquids of the absorbent of the invention; in addition, the flexibility of such an absorbent body may be adjusted according to the intended use.

As a basis for the matrix, both synthetic, water-soluble, film-forming polymers such as polyvinyl alcohols, polyalkyl allyl ethers, polyglycol ethers, polyvinylpyrrolidones, polyacrylates, polymethacrylates, as well as derivatives and copolymers thereof, and natural, water-soluble, film-forming polymers, such as guar, alginates, agar-agar, xanthan, pectin, and starch and the like, as well as chemically modified raw materials, such as ethers and/or esters and/or hydrolyzates and/or oxidation products of polysaccharides or proteins, such as cellulose, amylose, starch, or wheat gluten are possible, as are copolymerizates and/or graft polymerizates based on natural or synthetic polymers.

Not least, the selection of the matrix material depends on the intended end use. Due to the matrix material, the flexibility of the superabsorbent sheet may be varied within a wide range. In a given matrix, the flexibility of the superabsorbent sheet may also be varied by using additives such as plasticizers or plasticizing agents like 2-ethylhexanol, glycerol and phthalic esters, but also by using fillers, such as chalk, pigments and fibers.

The basis of the SAP employed may be both a synthetic material, such as a water-swellable polymer and/or copolymer based on (meth)acrylic acid, (meth)acrylonitrile, (meth)acrylamide, vinyl acetate, vinylpyrrolidone, vinylpyridine, maleic acid (anhydride), itaconic acid (anhydride), fumaric acid, vinylsulfonic acid, and the salts, amides, N-alkyl derivatives, N,N-dialkyl derivatives and esters of these polymerizable acids, and a material of native origin, such as products of guar seed meal, carboxymethylcellulose, xanthan, alginates, gum arabic, hydroxyethylcellulose, hydroxypropylcellulose, methylcellulose, starch and starch derivatives, as well as partially crosslinked products thereof. Likewise, mixtures or copolymerizates and/or graft polymerizates of the above-mentioned components may be used.

Preferred materials are partially neutralized, slightly crosslinked polymers and copolymers of acrylic acid and acrylamide, graft polymerizates of starch, as well as crosslinked starches and cellulose derivatives. Suitable products include, e.g., the commercially available FAVOR and Stockosorb® types of Chemische Fabrik Stockhausen GmbH, Germany.

The grain size distribution of the powdered superabsorbent polymer employed may vary within wide limits— grains ranging from 0.1 $\mu$m to up to 20,000 $\mu$m are possible. Preferred grain fractions are in the range of from 1 $\mu$m to up to 5,000 $\mu$m. Particularly preferred are grain fractions ranging from 20 to 1,000 $\mu$m.

The grain fraction of SAP, which is incorporated in the sheet, crucially depends on the intended end use of the film. While grain fractions of about 500 $\mu$m are normally used in diapers, grain fractions of about 1,000 $\mu$m are preferred in agriculture, and those around 100 $\mu$m and smaller are preferred in the cable industry.

According to the invention, the superabsorbent sheet is produced by combining the above-mentioned components. To this end, a viscous solution of the water-soluble polymer is applied on a sheet, such as a sheet metal, siliconized paper, or a PTFE film using suitable procedures, such as spraying, spreading and knife-coating.

The sheet may be a flat large-area structure as well as the surface of a sphere.

Subsequently, the water-soluble polymer on the sheet is sprinkled with a superabsorbent polymer. The product thus obtained is dried at suitable temperatures, i.e., at temperatures between those usually employed in freeze drying and 300° C., preferably at temperatures between 50° C. and 240° C., optionally under reduced pressure.

Microwave or freeze drying techniques may also be used to dry the sheet material.

During the production of the absorbent sheet materials, particularly in drying thereof, chemical or physical binding between the matrix material B and the absorbing component A may possibly occur. As an example of chemical binding, the esterification reaction should be mentioned here, which may occur between carboxyl and hydroxyl groups. Physical bonds result, e.g., from loop formation or entanglement of the polymer molecules at the surface region of component A or by interactions of functional groups of the polymer molecules in the components A and B.

After drying, the superabsorbent sheet material is removed from the auxiliary surface used.

According to the invention, another preferred production of the superabsorbent sheet is performed by sprinkling a film or some other sheet formed from the matrix material with an SAP, and subsequently moistening the mixture with water or an aqueous solution or some other solvent mixture, or by sprinkling a film or some other sheet formed from the matrix material with a moistened SAP and subsequently drying said sheet.

According to the invention, another preferred production of the superabsorbent sheet is performed by sprinkling a film or some other sheet formed from the matrix material with an SAP, and heating this mixture until the matrix material is softened. The sheet thus formed may then additionally be calendered to improve fixation of the superabsorbent polymer in the matrix. This process involves the precondition that the matrix material used be thermoplastic.

Another preferred production of an absorbent sheet material according to the invention is carried out by extruding the matrix material. The SAP in a suitable form (with respect to grain size and metering procedure) is added to the matrix material prior to, during, or after extrusion.

Then, a defined arrangement of the SAP in a sheet may also be obtained by extruding the matrix material together with the SAP into fibers, and subsequently arranging these fibers in a sheet-like manner by means of suitable methods (air stream, blow molding).

Such a defined arrangement may easily be realized during the production process by using a template, or by using specific sprinkling arrangements during application of the powdered superabsorbent polymer. Layering multiple superabsorbent sheets allows spatially defined absorber structures to be generated which, in addition, may have an absorption gradient.

Optionally, a sheet material according to the invention may also be formed directly during the production of a water-soluble film, which means that the superabsorber is directly incorporated in the sheet-like matrix during a suitable processing step in the production of same.

The ratio of superabsorbent polymer and matrix may be varied within wide limits; it may range between matrix:SAP=1:1,000 to 100:1. Ratios of matrix:SAP=1:100 to 10:1 are preferred, with ratios of matrix:SAP=1:25 to 2:1 being particularly preferred.

While in diaper construction, as a rule, high SAP and low matrix concentrations are desirable, lower SAP concentrations are frequently preferred in other fields for planting pots or inserts in foodstuff packagings. Thus, the SAP/matrix ratio essentially depends on the intended use.

The thickness of the absorbent sheet may be influenced by both the amount of matrix used and the particle size and amount of the SAP used. It may be between 0.2 $\mu$m and 30,000 $\mu$m; sheets having a thickness of from 1 to 6,000 $\mu$m are preferred; particularly preferred is a sheet thickness of between 20 $\mu$m and 2,000 $\mu$m. The thickness of the absorbent sheet must also be adapted to the intended end use. Thus, the layer thickness of a sheet intended for use in diaper constructions or feminine hygiene articles must be as thin as possible to increase the wearing property of the diaper. In the case of sheets intended for a depot formulation, a greater thickness may result in a desirable delay of depot material release.

Surprisingly, it was found that these sheets have an absorptive capacity for water or aqueous solutions, which is in accordance with the amount of incorporated superabsorbent material. There is no loss in absorptive capacity of the superabsorber as might be expected as a result of the presence of the matrix material. This applies to the overall absorption and the retention (absorption with subsequent pressure load) as well as the absorption during pressure load (absorption under load).

Surprisingly, it was also found that she absorption rate for water or aqueous solutions of such sheets depends on the ratio of matrix material and superabsorbent polymer. Consequently, the absorption rate may be controlled by the ratio SAP/matrix and, of course, by the type of matrix material as well, namely such that a higher matrix ratio results in a reduction of the absorption rate.

The superabsorbent sheets according to the invention meet the demand for a defined arrangement of the superabsorbent polymer on a sheet, which can advantageously be used in hygienic articles. The advantages of the defined arrangement of superabsorbers in hygienic articles have been described in EP 212,618 B1; they result, for example, from the fact that the liquid load in a diaper is not uniform. Thus, sites of high and low SAP concentrations are required in a diaper.

Test Methods:

Tea Bag Test (TBT)

To determine the absorptive capacity, the TBT was carried out. A 0.9% NaCl-solution was used as test solution (unless otherwise stated).

A piece of material containing about 0.2 g of SAP is punched out of the absorbing sheet. This piece is weighed into a tea bag. Subsequently, the tea bag is placed into the test solution for a defined period of time. After draining for 5 minutes, the tea bag was weighed out (determination of TBT max.) and subsequently, the tea bag was centrifuged in a centrifuge (commercially available spin dryer, 1,400 rpm). Thereafter, weighing is carried out again (determination of TBT ret.).

Using multiple tests employing the same material and varying immersion times, the absorption as a function of immersion time (absorption rate) of the superabsorbent sheet material for water or aqueous solutions can be determined. The absorption of liquid is calculated relative to either 1 g of sheet, 1 g of SAP employed, or 1 m² of sheet.

Absorption Under Load (AUL)

To determine the liquid absorption capacity under pressure, the "absorption under load" was determined as described in EP 339,461.

Departing from said procedure, a circular piece of the superabsorbent body having the size of the inner diameter of the AUL crucible was used as test substance. The absorption of liquid is calculated relative to either 1 g of body, 1 g of SAP employed, or 1 m² of body.

EXAMPLES 1–3

Figure 1:
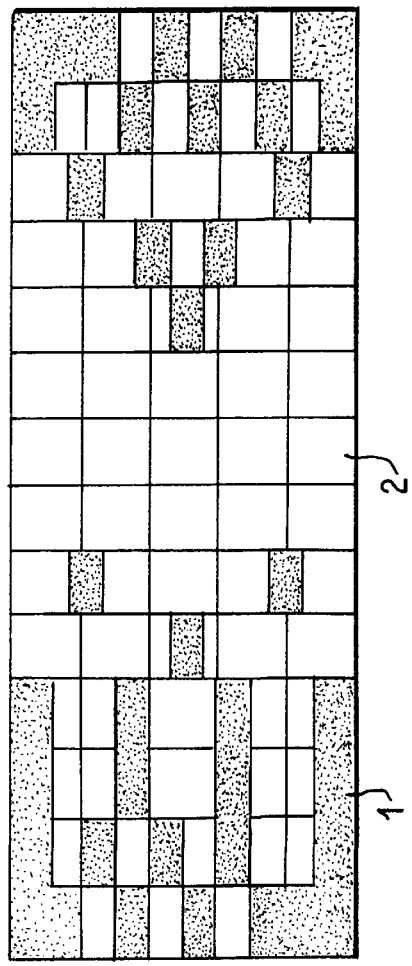
FIG. 1 Sprinkling frame
1—(bright area) penetrable part of the sprinkling frame
2—(dark area) impenetrable part of the sprinkling frame
FIG. 2 Diaper construction
1—Laminates of polypropylene covering fleece and polyethylene film
2—Leakage protection with incorporated rubber threads
3—Covering fleece made of polypropylene
4—Polyethylene film on the back side
5—Core envelope made of cellulose fibers
6—Core containing the superabsorbent sheet material The invention will be illustrated with reference to the following examples.

A highly viscous solution is prepared from 25 g of Vinol® 205 (water-soluble polyvinyl alcohol) and 75 g of deionized water. A part of this solution (cf., Table) is uniformly spread on a sheet (Teflon-coated film or the like) of 270 cm². The sheet thus formed is sprinkled with about 30 g of FAVOR® SXM 100 superabsorber (slightly crosslinked, partially neutralized polyacrylate) and then dried for 5 minutes at a temperature of 180° C. Subsequently, the unfixed part of the superabsorber is removed using a brush. Flexible, superabsorbent sheets are obtained which can easily be removed from the surface (Teflon-coated film).

TABLE 1

The Table shows the dependence of the absorption rate on the matrix:SAP ratio, a decreasing matrix ratio resulting in faster absorption.

| Ex. | Solution [g] | SAP [g/m²] | Vinol ®205 [g/m²] | TBT (30 sec.) max./ret. [g/g]/[g/g] | TBT (60 sec.) max./ret. [g/g]/[g/g] | TBT (30 min.)* max./ret. [g/g]/[g/g] |
|---|---|---|---|---|---|---|
| 1 | 10 | 226 | 93 | 6/6 | 9/9 | 50/31 |
| 2 | 5 | 182 | 46 | 7/7 | 12/12 | 50/31 |
| 3 | 2.5 | 203 | 23 | 9/9 | 13/13 | 50/31 |
| SXM 100 | 0 | — | 0 | 9/9 | 14/14 | 50/31 |

The TBT values marked with * relate to the amount of superabsorber used, the other TBT values relate to the weight per unit area.

EXAMPLE 4

The same procedure as in Example 2 is used, however, a solution of 1 g of Mowiol® 4/88 (water-soluble polyvinyl alcohol of Hoechst AG) and 3 g of water is charged on a sheet of 476 cm². After processing (cf., Examples 1–3) a flexible film is obtained having a superabsorber ratio of 189 g/m²; the ratio of Mowiol® 4/88 is 21 g/m².

TBT: max./ret. $[l/m^2]/[l/m^2]=9.4/5.8$; AUL $(2\times10^3$ Pa$)=5.7$ $l/m^2$.

EXAMPLE 5

The procedure is as in Example 4, however, Mowiol® 5/88 (water-soluble polyvinyl alcohol of Hoechst AG) is used instead of Mowiol® 4/88. After processing (cf., Examples 1–3) a flexible film is obtained which has a superabsorber ratio of 144 g/m²; the ratio of Mowiol® 5/88 is 21 g/m².

TBT: max./ret. $[l/m^2]/[l/m^2]=7.2/4.4$; AUL $(2\times10^3$ Pa$)=4.4$ $l/m^2$.

EXAMPLE 6

A solution of 200 g of deionized water, 50 g of glycerol, and 10 g of guar seed meal (type 104 of Roeper company) is stirred to make a homogeneous solution. The solution is spread on a sheet of 3,000 cm² and sprinkled with 100 g of FAVOR® SXM 100. The sheet is dried at 75° C. for 4 hours and subsequently, the non-adhering SAP is removed using a soft brush.

An absorbent sheet of moderate flexibility is obtained, having an SAP ratio of 200 g/m².

EXAMPLE 7

The procedure is as in Example 6, however, carboxymethylcellulose (type Walocel® 40000 of the Wolf Walsrode company) is used instead of guar seed meal. In addition, drying is effected at 130° C. for 30 minutes. The sheet thus obtained is flexible and has an SAP ratio of 180 g/m².

EXAMPLE 8

The procedure is as in Example 7, however, Acrakonz® BN (soluble, slightly crosslinked, anionic emulsion polymerizate based on acrylic acid derivatives of Chemische Fabrik Stockhausen GmbH) is used instead of carboxymethylcellulose. In accordance with the concentration of Acrakonz® BN, a correspondingly larger amount (24 g) of this product is used. The sheet thus obtained is flexible and has an SAP ratio of 240 g/m².

TABLE 2

The Table shows the dependence of the absorption rate on the type of matrix materials used

| Ex.-No. | SAP [g/m²] | TBT (30 sec.) max./ret. [g/g]/[g/g] | TBT (60 sec.) max./ret. [g/g]/[g/g] | TBT (300 sec.) max./ret. [g/g]/[g/g] |
|---|---|---|---|---|
| 6 | 200 | 6/6 | 15/15 | 21/16 |
| 7 | 180 | 7/7 | 10/10 | 13/13 |
| 8 | 240 | 5/5 | 10/8 | 18/15 |

The TBT values relate to the weight per unit area.

EXAMPLE 9

One square meter of a polyvinyl alcohol film (Reel L336; W/O 1483 of Aquafilm Ltd., 20 μm in thickness) is sprayed with 50 ml of a solution of 50% water and 50% ethyl alcohol and subsequently sprinkled with 400 g of FAVOR® SXM 100. The powder is slightly pressed against the surface. Thereafter, drying is effected for 5 minutes at 120° C.

The non-fixed portion of SXM 100 is removed using a vacuum cleaner; 113 g/m² remain.

TBT: max./ret. $[l/m^2]/[l/m^2]$=5.7/3.5; AUL $(2\times10^3$ Pa)= 3.5 $l/m^2$.

EXAMPLE 10

One square meter of a polyvinyl alcohol film (REEL L336; W/O 1483 of Aquafilm Ltd., 50 μm in thickness) is sprayed with 50 ml of a solution of 50% water and 50% ethyl alcohol and then sprinkled with 400 g of FAVOR® SXM 100. The powder is slightly pressed against the surface. Subsequently, drying is effected for 5 minutes at 120 C.

The non-fixed portion of SXM 100 is removed using a vacuum cleaner; 179 g/m² remain.

TBT: max./ret. $[l/m^2]/[l/m^2]$=8.9/5.5; AUL $(2\times10^3$ Pa)= 5.4 $l/m^2$.

EXAMPLE 11

A solution of 2 g of Vinol 205, 2 g of glycerol, and 6 g of water is distributed over a Teflon-coated film on an area of 14×44 cm. Then, a template (cf., FIG. 1) is placed thereon. The free areas are sprinkled with 9 g of Favor SXM 100. The sheet is dried for 5 minutes at 140° C. in a circulating air oven. Subsequently, it is sprayed with a solution of 0.25 g of Vinol 205, 0.25 g of glycerol, and 1.5 g of water. Then, drying is effected again under the above-mentioned conditions.

The sheet thus obtained is removed from the Teflon-coated film. It is flexible and has an absorptive capacity corresponding to that of the superabsorber used.

EXAMPLE 12

Example 11 is repeated; however, no glycerol is used. The resulting sheet is hard, brittle and scarcely flexible. It has an absorptive capacity corresponding to that of the superabsorber used.

EXAMPLE 13

A solution of 2 g of Vinol 205, 2 g of glycerol, and 6 g of water is distributed over a Teflon-coated film on an area of 14×44 cm. Then, a template (cf., FIG. 1) is placed thereon. The free areas are sprinkled with 6 g of Favor SXM 100. The sheet is dried for 5 minutes at 140° C. in a circulating air oven.

Subsequently, it is sprayed with a solution of 0.25 g of Vinol 205, 0.25 g of glycerol, and 1.5 g of water. Again, the template is placed thereon. The free areas are sprinkled with 4.5 g of Favor SXM 100. Subsequently, drying is effected again under the above-mentioned conditions.

Spraying, placing the template and SAP sprinkling are repeated once more, using 2.5 g of SAP.

Finally, spraying and drying are carried out once more. The sheet thus obtained is removed from the Teflon-coated film. It is flexible and has an absorptive capacity corresponding to that of the superabsorber arranged in all spatial directions in a defined manner.

EXAMPLE 14

One square meter of a polyvinyl alcohol film (Reel L336; W/O 1483 of Aquafilm Ltd., 20 μm in thickness) is sprinkled with 50 g of FAVOR® SXM 100. The powder is slightly pressed against the surface. Subsequently, a second film of the same material is placed thereon. The sheet is covered with a Teflon-coated film and ironed (the iron is set to 180° C.) until the PVA films and the superabsorber have melted into one another. The absorptive capacity of the sheet corresponds to the amount of SAP used.

EXAMPLE 15

Figure 2:
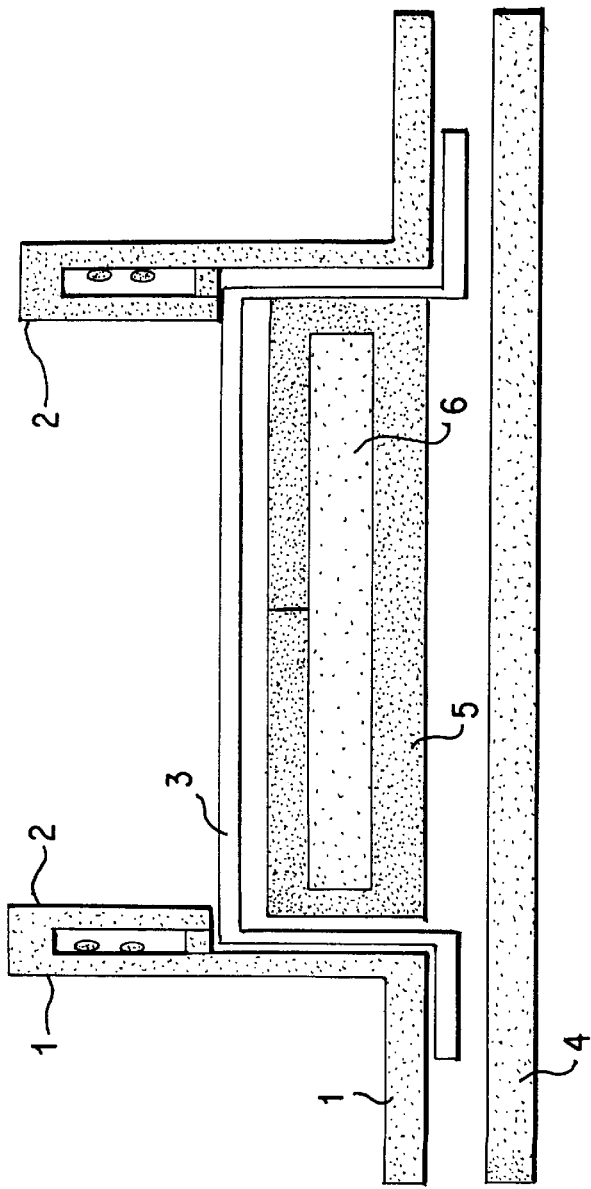

According to FIG. 2, a diaper is constructed using the film produced in Example 13. The PE film used and the polypropylene covering fleece are materials from a diaper production. The sheet produced in Example 13 is used as core (6).

EXAMPLE 16

10×15 cm of the sheet described in Example 2 is placed in a packaging pan and covered with a commercially available kitchen tissue (Kleenex). A deep-frozen chicken (850 g) is placed on the tissue. The entire thawed water (test period 18 h) is absorbed by the sheet of the invention.

EXAMPLE 17

Example 12 is repeated without a template. Instead of Favor, Stockosorb 400 (slightly crosslinked copolymer based on acrylamide) was used. Strips of 1×7.5 cm in size were cut from this sheet. Eight of the strips were completely inserted into a cylindrical flowerpot (height: 10 cm, diameter: 8.5 cm) containing soil. The soil is kept moist for 5 days. Thereafter, the film had dissolved, the SAP was in the soil in an arrangement suitable, e.g., for plant cultivation.

EXAMPLE 18

Example 1 is repeated; however, instead of Favor, the same amount of the superabsorbent depot agent formulation described in Example 9 of PCT/EP93/01060 is used.

1 cm² of the sheet thus obtained is welded in a tea bag. The tea bag is suspended in 50 ml of a 0.2% saline solution for one hour. The salt solution is renewed after one hour.

Even after the 5th cycle, the blue coloration of the saline solution indicates release of the active substance.

EXAMPLE 19

A sheet produced according to Example 10 is ironed according to the method described in Example 14 onto a fabric as used to sheathe cables. The composite of the sheet of the invention and the fabric has high mechanical stability, the fabric tape has retained its flexibility, the absorption corresponds to the SAP ratio.

FIG. 1 shows the template used in Example 11.

FIG. 2 shows the diaper construction of Example 15.

We claim:

1. A sheet-like absorbent for water or aqueous liquids, comprising:
    A) at least one water-swellable polymer, and
    B) at least one water-soluble polymer,
wherein component B forms a sheet-like matrix, and component A is incorporated in or attached to the matrix in a defined arrangement.

2. A sheet-like absorbent according to claim 1, wherein component A comprises at least one polymer or copolymer of at least one polymerizable monomer selected from the group consisting of acrylic acid, methacrylic acid, acrylonitrile, methacrylonitrile, acrylamide, methacrylamide, vinyl acetate, vinyl alcohol, vinylpyrrolidone, vinylpyridine, maleic acid, maleic anhydride, itaconic acid, itaconic anhydride, fumaric acid, vinylsulfonic acid, and amides, N-alkyl derivatives, N,N-dialkyl derivatives and esters thereof.

3. A sheet-like absorbent according to claim 1, wherein component A comprises at least one slightly cross-linked, natural polymer selected from the group consisting of guar seed meal, carboxymethylcellulose, xanthan, alginates, gum arabic, chitin, chltosan, agar-agar, hydroxyethylcellulose, hydroxypropylcellulose, methylcellulose, starch, and starch derivatives.

4. A sheet-like absorbent according to claim 3, wherein component A comprises a mixture of at least two of said polymers.

5. A sheet-like absorbent according to claim 1, wherein component B comprises at least one water-soluble polymer or copolymer of at least one polymerizable monomer selected from the group consisting of acrylic acid, methacrylic acid, acrylonitrile, methacrylonitrile, acrylamide, methacrylamide, vinyl acetate, vinyl alcohol, vinylpyrrolidone, vinylpyridine, maleic acid, maleic anhydride, itaconic acid, itaconic anhydride, fumaric acid, vinylsulfonic acid, and amides, N-alkyl derivatives, N,N-dialkyl derivatives and esters thereof.

6. A sheet-like absorbent according to claim 1, wherein component B comprises at least one soluble natural polymer selected from the group consiting of guar seed meal, carboxymethylcellulose, xanthan, alginates, gum arabic, chitin, chitosan, agar-agar, hydroxyethylcellulose, hydroxypropylcellulose, methylcellulose, starch, and starch derivatives.

7. A sheet-like absorbent according to claims 6, wherein component B comprises a mixture of at least two of said polymers.

8. A sheet-like absorbent according to claim 1, wherein components B and A are present in a ratio B:A of from 1:1,000 to 100:1.

9. A sheet-like absorbent according to claim 8, wherein components B and A are present in a weight ratio B:A of from 1:100 to 10:1.

10. A sheet-like absorbent according to claim 9, wherein components B and A are present in a weight ratio B:A of from 1:25 to 2:1.

11. A sheet-like absorbent according to claim 1, wherein components A and B are partially reacted chemically with each other.

12. A sheet-like absorbent according to claim 1, wherein the components A and B are only physically linked to each other.

13. A sheet-like absorbent according to claim 1, wherein said absorbent is in the form of a film, sheet, foil, rolled article, or a laminate.

14. A process for producing a sheet-like absorbent, said process comprising the steps of:
    forming a sheet-like matrix comprising at least one water-soluble polymer B; and
    incorporating or attaching a water-swellable polymer A to the matrix.

15. A process according to claim 14, comprising the steps of:
    a) preparing an aqueous solution of component B;
    b) applying the solution from step a) to a support;
    c) sprinkling the solution-covered support from step b) with component A to obtain a composite material, and
    d) drying the composite material from step c).

16. A process according to claim 14, wherein steps b) and c) are repeated.

17. A process according to claim 16, wherein steps b), c) and d) are repeated.

18. A process according to claim 15, wherein the absorbent is subjected to a final treatment consisting of steps b) and d).

19. A process according to claim 15, wherein in step b) the solution of component B is applied by spreading, knife-coating, spraying, pouring, lick-rolling or trickling.

20. A process according to claim 14, comprising the steps of:
    a) disposing a material of component A on a surface of a film of component B, and
    b) contacting the film with a solvent for component B so that the film is solubilized but not dissolved, and
    c) drying the resulting product.

21. A process according to claim 20, wherein the film of component B is first contacted with the solvent and then component A is sprinkled on the surface of the film.

22. A process according to claim 20, wherein steps a) and b) are repeated several times.

23. A process according to claim 20, wherein the absorbent are covered with a final film of component B.

24. A process according to claim 20, wherein the film is contacted with the solvent by applying the solvent by spreading, knife-coating, spraying, pouring, lick-rolling or trickling.

25. A process according to claim 15, comprising the steps of:
    a) mixing a solvent for component B with component A to form a mixture;
    b) contacting a film of component B with the mixture from step a) to obtain a composite product, and
    c) drying the composite product from step b).

26. A process according to claim 25, wherein steps a) and b) are repeated several times.

27. A process according to claim 25, further comprising the step of covering the dried product from step c) with a film of component B.

28. A process according to claim 15, comprising the steps of:
    a) sprinkling a film of component B with a polymer of component A, and
    b) thereafter fixing the polymer of component A to the film by application of heat, pressure or a combination of heat and pressure.

29. A process according to claim 28, wherein the product from step b) is covered with another film of component B and thereafter subjected to a heat treatment.

30. A process according to claim 28, wherein the polymer of component A is fixed to the film of component B by a heat treatment, further comprising the step of covering the fixed product from step b) with a film after said heat treatment.

31. A process according to claim 28, wherein steps a) and b) are repeated several times.

32. A process for producing a sheet-like absorbent comprising a matrix of at least one water soluble polymer B having incorporated therein at least one water-swellable polymer A, wherein the matrix is produced by extrusion and component A is incorporated in component B during the extrusion.

33. A process according to claim 32, wherein component A is sprinkled through a template, whereby component A is deposited in a pattern defined by said template.

34. A process according to claim 15, wherein component A is sprinkled through a template, whereby component A is deposited in a pattern defined by said template.

35. A method of absorbing an aqueous liquid, said method comprising contacting said liquid with an absorbent comprising a sheet-like matrix of at least one water-soluble polymer B having at least one water swellable polymer A incorporated therein or attached thereto.

36. A method according to claim 35, wherein said aqueous liquid is a body fluid.

37. A method according to claim 35, said method comprising incorporating said absorbent agent in a plant growth or storage medium, and moistening said medium, whereby moisture is retained in said medium.

38. A method according to claim 35, wherein said agent comprises an absorbent web, said method comprising wrapping said web around a pipe, wire or fiber optic cable, whereby said pipe, wire or fiber optic cable is insulated and shielded against moisture.

39. A method according to claim 35, wherein said agent comprises an absorbent web, said method comprising applying said web to an external wall of a building, whereby said wall is insulated and shielded against moisture.

40. A method according to claim 35, wherein said agent is a packaging material, said method comprising packing an article in said material, whereby the packed article is shielded against moisture.

41. A method according to claim 35, wherein said agent is incorporated in an article of clothing, whereby a wearer of said article of clothing is shielded against dampness.

42. A method according to claim 35, wherein said agent is a reservoir for controlled release of an aqueous fluid, said method comprising contacting said agent with said fluid and thereafter placing said agent in an environment to be supplied with said fluid, whereby said agent gradually releases said fluid into said environment.

43. A sheet-like absorbent according to claim 12, wherein the components A and B are physically linked by a physical bond selected from the group consisting of loop formation, entanglement of polymer molecules at a surface region of component A, and interaction of functional groups of components A and B.

* * * * *